(12) United States Patent
Chen et al.

(10) Patent No.: US 10,059,026 B2
(45) Date of Patent: Aug. 28, 2018

(54) PROCESS FOR TREATING WOOD

(71) Applicant: Dow Global Technologies LLC, Midland, MI (US)

(72) Inventors: Xue Chen, Manvel, TX (US); Stephen W. King, League City, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/315,217

(22) PCT Filed: Jun. 30, 2015

(86) PCT No.: PCT/US2015/038467
§ 371 (c)(1),
(2) Date: Feb. 27, 2017

(87) PCT Pub. No.: WO2016/003993
PCT Pub. Date: Jan. 7, 2016

(65) Prior Publication Data
US 2017/0274552 A1  Sep. 28, 2017

Related U.S. Application Data

(60) Provisional application No. 62/018,927, filed on Jun. 30, 2014.

(51) Int. Cl.
| | |
|---|---|
| *B27K 3/02* | (2006.01) |
| *B05D 7/06* | (2006.01) |
| *B27K 3/50* | (2006.01) |
| *B27K 3/15* | (2006.01) |
| *C08H 8/00* | (2010.01) |
| *C08L 23/14* | (2006.01) |
| *D21H 17/07* | (2006.01) |
| *D21H 17/35* | (2006.01) |
| *D21H 17/43* | (2006.01) |
| *B27K 3/08* | (2006.01) |
| *B27K 5/00* | (2006.01) |
| *B27K 3/36* | (2006.01) |
| *B27K 3/42* | (2006.01) |
| *B27K 3/34* | (2006.01) |
| *B27K 3/38* | (2006.01) |
| *A01N 33/02* | (2006.01) |
| *A01N 33/04* | (2006.01) |
| *A01N 27/00* | (2006.01) |
| *A01N 33/06* | (2006.01) |
| *B05D 1/36* | (2006.01) |
| *B05D 3/10* | (2006.01) |
| *B05D 5/00* | (2006.01) |
| *D06M 101/06* | (2006.01) |

(Continued)

(52) U.S. Cl.
CPC .............. *B27K 3/50* (2013.01); *A01N 27/00* (2013.01); *A01N 33/02* (2013.01); *A01N 33/04* (2013.01); *A01N 33/06* (2013.01); *B05D 1/36* (2013.01); *B05D 3/10* (2013.01); *B05D 3/107* (2013.01); *B05D 5/00* (2013.01); *B05D 7/06* (2013.01); *B27K 3/0278* (2013.01); *B27K 3/0292* (2013.01); *B27K 3/08* (2013.01); *B27K 3/153* (2013.01); *B27K 3/34* (2013.01); *B27K 3/36* (2013.01); *B27K 3/38* (2013.01); *B27K 3/42* (2013.01); *B27K 5/007* (2013.01); *B27K 5/0075* (2013.01); *C08H 8/00* (2013.01); *C08L 23/14* (2013.01); *D21H 17/07* (2013.01); *D21H 17/35* (2013.01); *D21H 17/43* (2013.01); *B05D 2203/20* (2013.01); *B05D 2507/00* (2013.01); *B05D 2507/005* (2013.01); *B05D 2507/01* (2013.01); *B05D 2507/015* (2013.01); *B05D 2507/02* (2013.01); *B05D 2507/025* (2013.01); *B27K 2240/20* (2013.01); *B27K 2240/70* (2013.01); *C08K 5/17* (2013.01); *C08K 5/18* (2013.01); *C08L 23/0876* (2013.01); *D06M 13/325* (2013.01); *D06M 15/227* (2013.01); *D06M 15/263* (2013.01); *D06M 15/267* (2013.01); *D06M 2101/06* (2013.01)

(58) Field of Classification Search
CPC ........ B27K 3/0278; B27K 3/08; B27K 3/153; B27K 3/34; B27K 3/36; B27K 3/38; B27K 3/42; B27K 3/50; B27K 5/007; B27K 5/0075; B27K 2240/20; A01N 27/00; A01N 33/02; A01N 33/04; A01N 33/06; B05D 1/36; B05D 3/10; B05D 3/107; B05D 5/00; B05D 7/06; B05D 2203/20; B05D 2507/00; B05D 2507/005; B05D 2507/01; B05D 2507/015; B05D 2507/02; B05D 2507/025
USPC ............ 106/15.05, 18.32; 428/541; 427/297, 427/333, 351, 408, 440
See application file for complete search history.

(56) References Cited

U.S. PATENT DOCUMENTS 3,389,109 A * 6/1968 Harmon ..................... C08J 3/07
523/332
3,891,470 A * 6/1975 Kotone ................... C23F 11/02
106/14.05

(Continued)

FOREIGN PATENT DOCUMENTS

| CH | 514411 A | * | 10/1971 |
| JP | 2014095173 A | * | 5/2014 |
| WO | 2007079213 A2 | | 7/2007 |

*Primary Examiner* — William P Fletcher, III

(57) ABSTRACT

The present disclosure describes a treated cellulosic material comprising: a cellulosic material having a porous structure defining a plurality of pores, at least a portion of the pores containing a treating agent comprising: a polymer comprising an olefin-carboxylic acid copolymer; and a modifying agent comprising a hydrophobic amine.

3 Claims, No Drawings

(51) Int. Cl.
*C08K 5/17* (2006.01)
*C08K 5/18* (2006.01)
*C08L 23/08* (2006.01)
*D06M 13/325* (2006.01)
*D06M 15/227* (2006.01)
*D06M 15/263* (2006.01)
*D06M 15/267* (2006.01)

(56) References Cited

U.S. PATENT DOCUMENTS

| | | |
|---|---|---|
| 4,737,491 A | 4/1988 | Leppavuori et al. |
| 4,857,322 A | 8/1989 | Goettsche et al. |
| 6,843,837 B2 | 1/2005 | Zhang et al. |
| 7,462,227 B2 | 12/2008 | Anderson et al. |
| 7,842,656 B2 | 11/2010 | Ashmore et al. |

* cited by examiner

PROCESS FOR TREATING WOOD

BACKGROUND OF THE INVENTION

Porous materials, such as cellulosic materials, need to be protected from mold growth, insect attack, rot and water impregnation to help preserve the physical properties of the cellulosic material. One example of such a cellulosic material is wood. A variety of treatment agents and preservation methods are known to preserve cellulosic materials.

Modern preservation methods typically involve pressure treating the cellulosic material with a treating agent. Pressure treatment typically allows the treating agent to penetrate throughout the porous structure of the cellulosic material. The treating agent is typically a chemical compound selected to impart the desired physical properties to the cellulosic material. For example, treating agents that increase hardness, add water resistance and improve the dimensional stability of the cellulosic material are of interest. Wood is capable of absorbing as much as 100% of its weight in water which causes the wood to swell, which after loss of water through evaporation causes the wood to shrink. This process of water absorption/evaporation is non-uniform and creates internal stresses in the wood leading to splitting, warping, bowing, crooking, twisting, cupping, etc. Also, water can serve as a pathway for organisms that degrade the cellulosic material, such as insects or fungus. Treating agents that repel insects, or minimize the formation of fungi/molds, or improve the overall durability of the cellulosic material are of interest. Further, treating agents can improve wind resistance, ultraviolet radiation resistance, stability at high and low temperatures, pest resistance, mold resistance, fire resistance and other issues which might affect the physical properties of the cellulosic material.

An improved treating agent for cellulosic materials is desired.

SUMMARY OF THE INVENTION

The present disclosure describes a treated cellulosic material comprising: a cellulosic material having a porous structure defining a plurality of pores, at least a portion of the pores containing a treating agent comprising: a polymer comprising an olefin-carboxylic acid copolymer; and a modifying agent comprising a hydrophobic amine.

The present disclosure further describes a method for preparing a treated cellulosic material comprising: (a) providing a cellulosic material; (b) a first treatment protocol comprising impregnating the cellulosic material with an aqueous dispersion comprising a polymer, the polymer comprising an olefin-carboxylic acid copolymer; and (c) a second treatment protocol comprising impregnating the cellulosic material with a modifying agent, the modifying agent comprising a hydrophobic amine

DETAILED DESCRIPTION OF THE INVENTION

As used herein, the term "porous material" refers to a material which is permeable such that fluids are movable therethrough by way of pores or other passages. An example of a porous material is a cellulosic material. Other examples of porous materials include stone, concrete, ceramics, and derivatives thereof. As used herein, the term "cellulosic material" refers to a material that includes cellulose as a structural component. Examples of cellulosic materials include wood, paper, textiles, rope, particleboard and other biologic and synthetic materials. As used herein, wood includes solid wood and all wood composite materials (e.g., chipboard, engineered wood products, etc.). Cellulosic materials generally have a porous structure that defines a plurality of pores.

As used herein, unless otherwise indicated, the phrase "molecular weight" refers to the nominal molecular weight.

A "treated cellulosic material" is a cellulosic material that has been treated with a treating agent to modify the properties of the cellulosic material. The properties modified by the treating agent include, but are not limited to, increased hydrophobicity, dimensional stability, fungi resistance, mold resistance, insect resistance, hardness, surface appearance, UV stability, fire resistance, and coatability. Increasing the hydrophobicity of a cellulosic material can provide other ancillary benefits, such as dimensional stability, by reducing the rate of water adsorption and evaporation, thus reducing the internal stresses of expanding and contracting.

A "treating agent" is a substance that, when combined with the cellulosic material, modifies the properties of the cellulosic material. In one instance, the treating agent comprises both a polymer and a modifying agent. The treating agent is applied to the cellulosic material. One method of applying the treating agent to the cellulosic material is through impregnation using pressure treatment. In one instance, the polymer is applied to the cellulosic material as part of a dispersion. Other methods of applying the treating agent are known, such as brushing, coating, spraying, dipping, soaking and extrusion. Once applied, the treating agent will permeate at least a portion of the pores of the cellulosic material.

As used herein, polymer refers to a molecule that is formed from one or more types of monomers. The polymer is preferably a copolymer or a mixture of copolymers and polymers. As used herein, copolymer may refer to an alternating copolymer, a periodic copolymer, a statistical copolymer, a random copolymer, a block copolymer, a graft copolymer, or other copolymer as is known. As used herein, copolymer refers to a polymer formed by uniting two or more monomers. Examples of copolymers include bipolymers, terpolymers, tetrapolymers, and other higher-ordered copolymers. In one instance, the polymer comprises an olefin-carboxylic acid copolymer. In one instance, the olefin-carboxylic acid copolymer comprises a monomer selected from the group comprising ethylene, propylene, 1-butene, 3-methyl-1-butene, 4-methyl-1-pentene, 3-methyl-1-pentene, 1-heptene, 1-hexene, 1-octene, 1-decene, 1-dodecene, butadiene, styrene, (meth)acrylic acid, maleic acid, maleic anhydride, or a mixture thereof. In one instance, a styrene acrylic acid dispersion is suitable, for example, Orotan™ CA-2005, commercially available from The Dow Chemical Company. Other suitable polymers and/or copolymers present in the mixture include elastomers, plastics and fibers.

In certain embodiments, the polymer comprises a polar olefin polymer, having a polar group as either a comonomer or grafted monomer. As used herein, a polar olefin polymer is an olefin (co)polymer which contains one or more polar groups. In exemplary embodiments, the polymer may, for example, comprise one or more polar polyolefins, having a polar group as either a comonomer or grafted monomer. Examples of polar groups include carboxylic acids, carboxylic acid anhydrides, carboxylic acid esters, carboxylic acid salts, and carboxylic acid amides. Exemplary polar polyolefins include, but are not limited to, ethylene/acrylic acid (EAA) and ethylene/methacrylic acid (EMAA) copolymers, such as those available under the trademarks PRIMA- COR™, commercially available from The Dow Chemical Company, NUCREL™, commercially available from E.I. DuPont de Nemours, and ESCOR™, commercially available from ExxonMobil Chemical Company. Exemplary copolymers also include ethylene/maleic anhydride copolymer, such as those available from The Dow Chemical Company under the trademark AMPLIFY™ GR. Exemplary copolymers further include ethylene/maleic anhydride and propylene/maleic anhydride copolymers, such as those available from Clariant International Ltd. under the trademark LICOCENE™. Other exemplary base polymers include, but are not limited to, ethylene/vinyl acetate copolymer, ethylene/ethyl acrylate (EEA) copolymer, ethylene/methyl methacrylate (EMMA) copolymer, and ethylene butyl acrylate (EBA) copolymer.

Other olefin-carboxylic acid copolymers may also be used as the polymer. Copolymers which have ester or anhydride functionalities can be converted to carboxylic acids or the polymer could also be derived by chemical modification of functional carboxylic acid salts by methods known to one skilled in the art. The polymer can also be modified to form other functional groups such as esters or amides and the like. Those having ordinary skill in the art will recognize that a number of other useful polymers may also be used.

In one embodiment, the base polymer may, for example, comprise a polar polyolefin selected from the group consisting of ethylene/acrylic acid (EAA) copolymer, ethylene/methacrylic acid copolymer (EMAA), and combinations thereof. In one instance, the polymer comprises ethylene/(meth)acrylic acid copolymer either alone, or in a mixture with other polymers or copolymers.

As used herein, the use of the term "(meth)" followed by another term such as acrylate refers to both acrylates and methacrylates. For example, the term "(meth)acrylate" refers to either acrylate or methacrylate; the term "(meth)acrylic" refers to either acrylic or methacrylic; and the term "(meth)acrylic acid" refers to either acrylic acid or methacrylic acid.

In one instance, the polymer is a constituent part of an aqueous dispersion. In one instance, the dispersion is a medium that comprises the polymer, water and one or more organic solvents. The aqueous dispersion is prepared such that the suspended particle size in the dispersion is suitable for penetrating the pores of the cellulosic material for distribution through the cellulosic material. In one instance, the dispersion also comprises one or more additives. In one instance, any solids present in the aqueous dispersion are held in a stable suspension and are transportable by the dispersion into the pores of the cellulosic material. In one instance, the solid content of the dispersion is 1 to 75 weight percent. In one instance the organic solvent is an oxygenated solvent, a hydrocarbon solvent, a halogenated solvent, or a combination thereof.

The carboxylic acid portion of the polymer is neutralized with a neutralizing agent at least in part to form a stable aqueous dispersion. As used herein, a neutralizing agent is any material in which the reaction with the carboxylic acid can potentially result in the formation of a salt. In one instance the neutralizing agent is selected from the hydroxides of alkali metals, ammonia or organic derivatives thereof (including amines). In one instance the neutralizing agent is a strong base or a weak base. For example, the neutralizing agent may be sodium hydroxide, potassium hydroxide, or ammonia or an amine, such as monoethanolamine (MEA), triethanolamine (TEA), diethylethanolamine (DEEA) or dimethylaminoethanol (DMEA). AQUACER™ 8804, available from BYK USA Inc., is an example of a neutralized EAA dispersion. A stable dispersion is a dispersion that is suitable for penetrating the pores of the cellulosic material. The neutralizing agent neutralizes at least a portion of the carboxylic acid groups of the polymer. As used herein, neutralization of the carboxylic acid groups refers to any reaction in which the hydrogen of the carboxylic acid group is transferred. In one instance, 5 to 100 mole percent of the carboxylic acid groups of the polymer are neutralized by the neutralizing agent. In another instance 10 to 80 mole percent of the carboxylic acid groups are neutralized by the neutralizing agent. In still another instance 20 to 70 mole percent of the carboxylic acid groups are neutralized by the neutralizing agent.

The modifying agent is a substance that, when combined with the polymer modifies at least a portion of the carboxylic acid groups of the polymer. In one instance, the modifying agent is a hydrophobic amine, for example, a primary, a secondary or a tertiary amine In one instance, the modifying agent is a hydrophobic amine salt. In one instance the hydrophobic amine contains only one amino group. The hydrophobic amine may be any suitable amine, such as a linear amine, a branched aliphatic amine, a cyclic amine, an aromatic amine, or a mixture thereof. The amine is selected such that the viscosity is low enough to penetrate the pores of the cellulosic material and contains six or more carbon atoms to provide sufficient hydrophobicity. In the case of highly viscous amines or solid amines, a solvent may be used, for example, water, oxygenated solvents, halogenated solvents, aromatic solvents, or hydrocarbons. Examples of hydrophobic amines include N-methyl N-hexyl amine, N,N-diethyl n-hexylamine, n-octylamine, n-decylamine n-dodecylamine, N-methyl cyclohexylamine, N,N,-diethyl cyclohexylamine, dicyclohexylamine, benzylamine, cocoamine, oleylamine, stearylamine, and the N,N-dimethyl substituted fatty amines. In one example, the modifying agent is phenethylamine or tallowamine. In one example, the modifying agent is polyetheramine (e.g., JEFFAMINE® M-2005 or JEFFAMINE® M-600 purchased from Huntsman Company)

The treating agent is combined with the cellulosic material. In one instance, the treating agent is introduced to the cellulosic material by pressure treatment, as described herein. In another instance, the treating agent is introduced to the cellulosic material by other techniques known in the art, for example, brushing, coating, dipping, soaking, spraying, and extrusion. The treating agent becomes impregnated in at least a portion of the pores of the cellulosic material, and thereby increases the weight of the cellulosic material. In one instance, the polymer increases the weight of the cellulosic material by 1 to 80 percent (as calculated after drying the cellulosic material). In one instance, the treating agent—the combination of the polymer and the modifying agent—increases the weight of the cellulosic material by 5 to greater than 100 percent (as calculated after drying the cellulosic material).

In one instance, the treating agent comprises one or more additives. The additive may be included as part of the dispersion, as part of the modifying agent, or may be included separately therefrom. Additives which are known to add properties to treated cellulosic materials are suitable, such as, flame retardants, dispersants and/or dyes. For example, the additives may be organic compounds, metallic compounds, or organometallic compounds. In one instance, the additive is a material which improves the wetting or penetration of the polymer into the wood, for example, solvents or surfactants (anionic, cationic or nonionic) that are stable in the dispersion. Examples of additives include, solvents, fillers, thickeners, emulsifiers, dispersing agents, buffers, pigments, penetrants, antistatic agents, odor substances, corrosion inhibitors, preservatives, siliconizing agents, rheology modifiers, anti-settling agents, anti-oxidants, other crosslinkers (e.g. diols and polyols), optical brighteners, waxes, coalescence agents, biocides and antifoaming agents. Such waxes may include petroleum waxes, paraffin waxes, a natural wax, or a synthetic wax such as polyethylene wax or oxidized polyethylene wax, beeswax, or slack wax. In addition, the treating agent may be used in conjunction with wood preservatives containing, for example, cupric-ammonia, cupric-amine, cupric-ammonia-amine complexes, quaternary ammonium compounds, or other systems. For example, the treating agent may be used with Alkaline Copper-Quaternary ammonium (ACQ) preservative systems. The treating agent may also be used with wood preservative technologies which use zinc salts or boron containing compounds. Optionally, other additives such as insecticides, termiticides, fungicides, and moldicides may be added to the treating agent. In one instance, the additive is included as part of the dispersion and forms a stable suspension therewith. In one instance, one or more surfactant is added to the dispersion. In one instance, a surfactant is selected which reduces gelling of the polymer at the surface of the cellulosic material. In one instance, a surfactant is selected which increases the amount of polymer impregnated in the cellulosic material. For example, suitable surfactants may be nonionic, anionic, or cationic. Examples of nonionic surfactants include: alkoxylated alcohols, alkoxylated alkyl phenols, fatty acid esters, amine and amide derivatives, alkylpolyglucosides, ethylene oxide/propylene oxide copolymers, polyols and alkoxylated polyols. For example, a nonionic surfactant is TERGITOL™ L-62, commercially available from The Dow Chemical Company. Examples of anionic surfactants include: alkyl sulfates, alkyether sulfates, sulfated alkanolamides, alpha olefin sulfonates, lignosulfonates, sulfosuccinates, fatty acid salts, and phosphate esters. For example, an anionic surfactant is DOWFAX™ C10L, commercially available from the Dow Chemical Company. Examples of cationic surfactants include alkyltrimethylammonium salts.

In one instance, the cellulosic material is prepared as a treated cellulosic material by pressure treatment. The pressure used to pressure treat the cellulosic material may be either higher or lower than atmospheric pressure. In one instance, the pressure is lower than ambient pressure, for example, 0.0001 to 0.09 MPa (0.75 to 675 mmHg). In another instance, the pressure is greater than ambient pressure, for example, 0.1 to 1.7 MPa (750 to 12750 mmHg). It is envisioned that pressure treatment processes known in the art are suitable for impregnating the cellulosic material with the treating agent.

In one instance, the cellulosic material is prepared as a treated cellulosic material by pressure treatment. The pressure used to pressure treat the cellulosic material may be either higher or lower than atmospheric pressure. In one instance, the pressure is lower than ambient pressure, for example, 0.0001 to 0.09 MPa (0.75 to 675 mmHg). In another instance, the pressure is greater than ambient pressure, for example, 0.1 to 1.7 MPa (750 to 12750 mmHg). It is envisioned that pressure treatment processes known in the art are suitable for impregnating the cellulosic material with the treating agent.

In one instance, the treated cellulosic material is prepared according to at least a first treatment protocol and a second treatment protocol. In one instance, the first treatment protocol comprises impregnating the cellulosic material with the polymer. The first treatment protocol comprises one or more of the following steps: (a) depositing the cellulosic material in a vessel; (b) holding the vessel at vacuum for 5 to 60 minutes; (c) introducing the polymer to the vessel; (d) pressurizing the vessel to 1.03 MPa for 5 to 60 minutes; (e) draining the excess polymer; (f) optionally removing excess polymer by vacuum and (g) air drying the cellulosic material at 20 to 60° C. for 24 to 48 hours. In one instance, the polymer is part of the aqueous dispersion.

In one instance, the product of the first treatment protocol is subsequently prepared according to a second treatment protocol that impregnates the cellulosic material with the modifying agent. The second treatment protocol comprises one or more of the following steps: (a) depositing the cellulosic material prepared according to the first treatment protocol in a vessel; (b) introducing the modifying agent to the vessel; (c) holding the vessel at either vacuum or increased pressure for 5 to 60 minutes; (d) optionally removing excess modifying agent by vacuum; and (e) air drying the cellulosic material at 60° C. for 24 to 48 hours.

In one instance, the product of the second treatment protocol is subsequently neutralized according to a neutralization protocol that neutralizes any residual modifying agent from the second treatment protocol by the use of a modifying agent neutralizer. In one instance, the modifying agent neutralizer is any material suitable for reacting with the modifying agent to reduce its basicity, for example, the dispersion. The neutralization protocol comprises one or more of the following steps: (a) depositing the cellulosic material prepared according to the second treatment protocol in a vessel; (b) introducing the modifying agent neutralizer to the vessel for 30 minutes; and (c) air drying the cellulosic material at 60° C. for 24 to 48 hours.

The several drying steps may be performed at a range of temperatures, whereby the duration of the air drying step is proportional to the temperature. Suitable air-drying temperatures are between room temperature (roughly 20° C.) and 180° C. The drying may be performed in air, in nitrogen, or other suitable atmosphere.

A water immersion test is used to determine the water repellency of the treated cellulosic material according to the American Wood Protection Association Standard E4-11 procedure (Standard Method of Testing Water Repellency of Pressure Treated Wood). The water immersion test involves first, providing both a treated wafer, comprising a treated cellulosic material prepared as described herein, and a control wafer, comprising a cellulosic material treated according to the first treatment protocol described herein except that the dispersion is replaced by distilled water; second, measuring the tangential dimension of both the treated wafer and the control wafer to provide an initial tangential dimension ($T_1$) (where the tangential dimension is perpendicular to the direction of the grain of the cellulosic material); third, placing both the treated wafer and the control wafer in a conditioning chamber maintained at 65±3% relative humidity and 21±3° C. until a constant weight is achieved; fourth, immersing both the treated wafer and the control wafer in distilled water at 24±3° C. for 30 minutes; and fourth, measuring the tangential dimension of both the treated wafer and the control wafer following removal from the water to provide a post tangential dimension ($T_2$).

DoN refers to the degree of neutralization of the carboxylic acid functionality in the polymer.

The percent swelling (S) for each individual wafer (both the treated wafer and the control wafer) is calculated as:

$$S(\%) = \frac{T_2 - T_1}{T_1} \times 100$$

In each of the Examples herein, the percent swelling of the control wafer is 4.7%.

Water-repellency efficiency (WRE) is used to determine the effectiveness of the treating agent in adding water repellant properties to the treated cellulosic material. WRE is calculated as:

$$WRE(\%) = \frac{S_1 - S_2}{S_1} \times 100$$

$S_1$ refers to the percent swelling of the untreated wafer; $S_2$ refers to the percent swelling of the treated wafer. According to E4-11, for most outdoor applications a minimum WRE of 75% is preferred.

The hardness of the treated cellulosic material is determined according to the Shore (Durometer) test using a Type D Durometer (30° cone, 1.40 mm diameter, 2.54mm extension, 44.48N spring force). Hardness is determined using the Type D Durometer by placing the cellulosic material on a hard flat surface, and the foot of the durometer is pressed with the given spring force against the cellulosic material. The hardness value is recorded from the gauge on the Durometer within one second of contact with the cellulosic material. At least five hardness tests were performed per sample of cellulosic material. Hardness values reported herein are averages of the tests performed for a given cellulosic material. The hardness value of an untreated wafer is 40.

The following Examples illustrate certain aspects of the present disclosure, but the scope of the present disclosure is not limited to the following Examples.

The dispersions in the following Examples were made by combining the polymer with the given amount of base in a mixed, pressurized vessel at 120° C. as is known in the art (for example, a suitable dispersion may be prepared according to "Preparation of Aqueous Dispersions of PRIMACOR Copolymers" from The Dow Chemical Company). All the vacuum operations in the examples are in the range of −0.00399 MPa to −0.00267 MPa.

EXAMPLE 1

A pine wafer (southern yellow pine, 4 cm×2 cm×0.5 cm) is held at the bottom of a Parr reactor by a weight (here a ring is used). The reactor pressure is set to vacuum for 30 minutes. 80 ml of a dispersion comprising 20 percent by weight PRIMACOR™ 5980i (50% DoN with MEA, 8.21 pH, particle size of 117 nm, 19% solid concentration) and 80 percent by weight water is introduced to the reactor. The reactor pressure is then set to 1.03 MPa for 60 minutes under nitrogen. The wafer is then placed in an oven and air dried at 60° C. for 48 hours. The wafer is held at the bottom of the reactor by the weight. The reactor is filled with sufficient phenethylamine (PEA) to submerge the wafer. The reactor pressure is set to vacuum for 60 minutes. The wafer is then placed in an oven and air dried at 60° C. for 48 hours, thereby providing a treated wafer. The treated wafer and a control wafer are each processed according to the E4-11 procedure. The percent swelling for the first piece of the wafer is 0.27%; the WRE of the first piece of the wafer is 94.1%. The hardness of the treated wafer is measured as 57.9 using a Type D Durometer.

EXAMPLE 2

A pine wafer (southern yellow pine, 4 cm×2 cm×0.5 cm) is held at the bottom of a Parr reactor by a weight (here a ring is used). The reactor pressure is set to vacuum for 30 minutes. 80 ml of a dispersion comprising 20 percent by weight PRIMACOR™ 5980i (50% DoN with MEA, 8.21 pH, particle size of 117 nm, 19% solid concentration) and 80 percent by weight water is introduced to the reactor. The reactor pressure is then set to 1.03 MPa for 60 minutes under nitrogen. The wafer is then placed in an oven and air dried at 60° C. for 48 hours. The wafer is held at the bottom of the reactor by the weight. The reactor is filled with sufficient tallowamine (30% by weight tallowamine in 2-butoxyethanol) to submerge the wafer. The reactor pressure is set to vacuum for 60 minutes. The wafer is then placed in an oven and air dried at 60° C. for 48 hours, thereby providing a treated wafer. The wafer and a control wafer are each processed according to the E4-11 procedure. The percent swelling for the treated wafer is 0.87%; the WRE of the treated wafer is 80.9%. The hardness of the treated wafer is measured as 51.0 using a Type D Durometer.

EXAMPLE 3

A pine wafer (southern yellow pine, 4 cm×2 cm×0.5 cm) is held at the bottom of a Parr reactor by a weight (here a ring is used). The reactor pressure is set to vacuum for 30 minutes. 80 ml of a dispersion comprising 20 percent by weight PRIMACOR™ 5980i (50% DoN with TEA, 20% solid concentration) and 80 percent by weight water is introduced to the reactor. The reactor pressure is then set to 1.03 MPa for 60 minutes under nitrogen. The wafer is then placed in an oven and air dried at 60° C. for 48 hours. The wafer is held at the bottom of the reactor by the weight. The reactor is filled with sufficient phenethylamine (PEA) to submerge the wafer. The reactor pressure is set to vacuum for 60 minutes. The first piece of the wafer is then placed in an oven and air dried at 60° C. for 48 hours, thereby providing a treated wafer. The treated wafer and a control wafer are each processed according to the E4-11 procedure. The percent swelling for the treated wafer is 0.95%; the WRE of the treated wafer is 78.52%. The hardness of the treated wafer is measured as 55.2 using a Type D Durometer.

EXAMPLE 4

A pine wafer (southern yellow pine, 4 cm×2 cm×0.5 cm) is held at the bottom of a Parr reactor by a weight (here a ring is used). The reactor pressure is set to vacuum for 30 minutes. 80 ml of a dispersion comprising 20 percent by weight PRIMACOR™ 5990 (100% DoN with DMEA, 9.52 pH, 20% solid concentration) and 80 percent by weight water is introduced to the reactor. The reactor pressure is then set to 1.03 MPa for 60 minutes under nitrogen. The wafer is then placed in an oven and air dried at 60° C. for 48 hours. The wafer is held at the bottom of the reactor by the weight. The reactor is filled with sufficient phenethylamine (PEA) to submerge the wafer. The reactor pressure is set to vacuum for 60 minutes. The wafer is then placed in an oven and air dried at 60° C. for 48 hours, thereby providing a treated wafer. The treated wafer and a control wafer are each processed according to the E4-11 procedure. The percent swelling for the treated wafer is 0.7%; the WRE of the treated wafer is 85.03%. The hardness of the treated wafer is measured as 56.5 using a Type D Durometer.

EXAMPLE 5

A pine wafer (southern yellow pine, 4 cm×2 cm×0.5 cm) is held at the bottom of a Parr reactor by a weight (here a ring was used). The reactor pressure is set to vacuum for 30 minutes. 80 ml of a dispersion comprising 10 percent by weight PRIMACOR™ 5990i (60% DoN with MEA), 6 wt % TERGITOL™ L-62, and 84% water is introduced to the reactor. TERGITOL™ L-62 is a nonionic surfactant manufactured by The Dow Chemical Company. The reactor pressure is then set to 1.03 MPa for 60 minutes under nitrogen. The wafer is then placed in an oven and air dried at 60° C. for 48 hours, thereby providing a treated wafer. The weight gain of the wood after treatment is 30%. The treated wafer and the control wafer are each processed according to the E4-11 procedure. The percent swelling for the treated wafer is 4.5%; the WRE of the treated wafer is 3.5%. The hardness of the treated wafer is measured as 45.2 using a Type D Durometer.

EXAMPLE 6

A pine wafer (southern yellow pine, 4 cm×2 cm×0.5 cm) is held at the bottom of a Parr reactor by a weight (here a ring was used). The reactor pressure is set to vacuum for 30 minutes. 80 ml of a dispersion comprising 20 percent by weight PRIMACOR™ 5990i (60% DoN with MEA, 10% solid concentration) and 80 percent by weight water is introduced to the reactor. The reactor pressure is then set to 1.03 MPa for 60 minutes under nitrogen. The wafer is then placed in an oven and air dried at 60° C. for 48 hours, thereby providing a treated wafer. The weight gain of the wood after treatment is 19%. The treated wafer and the control wafer are each processed according to the E4-11 procedure. The percent swelling for the treated wafer is 4.2%; the WRE of the treated wafer is 10.1%. The hardness of the treated wafer is measured as 45.0 using a Type D Durometer.

EXAMPLE 7

A pine wafer (southern yellow pine, 4 cm×2 cm×0.5 cm) is held at the bottom of a Parr reactor by a weight (here a ring is used). The reactor pressure is set to vacuum for 30 minutes. 80 ml of a dispersion comprising 94 percent by weight PRIMACOR™ 5980i aqueous dispersion (60% DoN with TEA, 7.8 pH, particle size of 18.5 nm, 24% solid concentration) and 6 percent by weight DOWFAX™ C10L is introduced to the reactor. The reactor pressure is then set to 1.03 MPa for 60 minutes under nitrogen. The wafer is then placed in an oven and air dried at 60° C. for 48 hours. The wafer is held at the bottom of the reactor by the weight. The reactor is filled with sufficient 10 wt % JEFFAMINE® M-2005 aqueous solution to submerge the wafer. The JEFFAMINE® M-2005 polyetheramine purchased from Huntsman Company, is a nominal 2000 molecular weight monoamine with a PO/EO ratio of about 29/6. The reactor pressure is set to 150 psi for 60 minutes. The wafer is then placed in an oven and air dried at 60° C. for 48 hours, thereby providing a treated wafer. The treated wafer and a control wafer are each processed according to the E4-11 procedure. The percent swelling for the first piece of the wafer is 0.8%; the WRE of the first piece of the wafer is 82.7%. The hardness of the treated wafer is measured as 53.9 using a Type D Durometer.

EXAMPLE 8

A pine wafer (southern yellow pine, 4 cm×2 cm×0.5 cm) is held at the bottom of a Parr reactor by a weight (here a ring is used). The reactor pressure is set to vacuum for 30 minutes. 80 ml of a dispersion comprising 94 percent by weight PRIMACOR™ 5980i aqueous dispersion (60% DoN with TEA, 7.8 pH, particle size of 18.5 nm, 24% solid concentration) and 6 percent by weight DOWFAX™ C10L is introduced to the reactor. The reactor pressure is then set to 1.03 MPa for 60 minutes under nitrogen. The wafer is then placed in an oven and air dried at 60° C. for 48 hours. The wafer is held at the bottom of the reactor by the weight. The reactor is filled with sufficient 10 wt % JEFFAMINE® M-600 aqueous solution to submerge the wafer. The JEFFAMINE® M-600 polyetheramine purchased from Huntsman Company is 600 molecular weight polypropylene glycol monoamine, with methoxyethyl termination at the other end. The reactor pressure is set to 150 psi for 60 minutes. The wafer is then placed in an oven and air dried at 60° C. for 48 hours, thereby providing a treated wafer. The treated wafer and a control wafer are each processed according to the E4-11 procedure. The percent swelling for the first piece of the wafer is 2.2%; the WRE of the first piece of the wafer is 52.8%. The hardness of the treated wafer is measured as 52.2 using a Type D Durometer.

The Examples illustrate that when the cellulosic material contains the treating agent, including both the polymer and the modifying agent, favorable WRE results are obtained. However, where the cellulosic material has not been treated by both the polymer and the modifying agent, such as in Comparative Examples 5 and 6, favorable WRE results are not obtained.

What is claimed is:

1. A method for preparing a treated cellulosic material comprising:
    (a) providing a cellulosic material, the cellulosic material comprising wood;
    (b) a first treatment protocol comprising impregnating the cellulosic material with an aqueous dispersion comprising a polymer, the polymer comprising an olefin-carboxylic acid copolymer wherein at least a portion of the carboxylic acid groups of the copolymer are neutralized; and
    (c) a second treatment protocol comprising impregnating the cellulosic material with a modifying agent comprising N-methyl N-hexylamine, N,N-diethyl n-hexylamine, n-octylamine, n-decylamine n-dodecylamine, N-methyl cyclohexylamine, N,N,-diethyl cyclohexylamine, dicyclohexylamine, benzylamine, cocoamine, oleylamine, stearylamine, an N, N-dimethyl substituted fatty amine, phenethylamine or tallowamine.

2. The method of claim 1, wherein the impregnating of the first treatment protocol is conducted wider pressure greater than or lower than ambient.

3. The method of claim 1, wherein the polymer is ethylene-acrylic acid copolymer.

* * * * *